US012740944B2

(12) United States Patent
Solorio et al.

(10) Patent No.: US 12,740,944 B2
(45) Date of Patent: Sep. 22, 2026

(54) FORMULATION TO DETER ABUSE OF DRUGS BY SMOKING

(71) Applicant: Purdue Research Foundation, West Lafayette, IN (US)

(72) Inventors: Luis Solorio, West Lafayette, IN (US); Anastasiia Vasiukhina, West Lafayette, IN (US); Yoon Yeo, West Lafayette, IN (US); Sheryhan F. Gad, Lawrence, KS (US)

(73) Assignee: Purdue Research Foundation, West Lafayette, IN (US)

( * ) Notice: Subject to any disclaimer, the term of this patent is extended or adjusted under 35 U.S.C. 154(b) by 514 days.

(21) Appl. No.: 18/134,109

(22) Filed: Apr. 13, 2023

(65) Prior Publication Data

US 2023/0414514 A1 Dec. 28, 2023

Related U.S. Application Data

(60) Provisional application No. 63/354,260, filed on Jun. 22, 2022.

(51) Int. Cl.
*A61K 9/16* (2006.01)
*A61K 9/00* (2006.01)

(52) U.S. Cl.
CPC .......... *A61K 9/1647* (2013.01); *A61K 9/0073* (2013.01)

(58) Field of Classification Search
CPC ............................ A61K 9/1647; A61K 9/0073
See application file for complete search history.

(56) References Cited

U.S. PATENT DOCUMENTS 5,538,739 A * 7/1996 Bodmer ................. A61K 38/31 424/501
8,637,540 B2 1/2014 Kumar et al.
2015/0110879 A1* 4/2015 Breder ................... A61K 45/06 424/490
2018/0185354 A1* 7/2018 Haswani .............. A61K 31/485

OTHER PUBLICATIONS

Kamaly et al; Degradable controlled-release polymers and polymeric nanoparticles: mechanisms of controlling drug release; Chem review, Feb. 24, 2016: 116(4): 2602-2663). (Year: 2016).*

Omidian, A., et al., "Routes of Opioid Abuse and its Novel Deterrent Formulations", J Develop Drugs 2015, vol. 4, Issue 5, 141, 7 pages, doi:10.4172/2329-6631.1000141.

Park, Kinman, et al., "Prevention of Opioid Abuse and Treatment of Opioid Addiction: Current Status and Future Possibilities", Annual Review of Biomedical Engineering, vol. 21:61-84 (vol. publication date Jun. 2019), First published as a Review in Advance on Feb. 20, 2019, https://doi.org/10.1146/annurev-bioeng-060418-052155.

Schaeffer, Tammi, "Abuse-Deterrent Formulations, an Evolving Technology Against the Abuse and Misuse of Opioid Analgesics", J. Med. Toxicol. (2012) 8, pp. 400-407, DOI 10.1007/s13181-012-0270-y.

* cited by examiner

*Primary Examiner* — Mina Haghighatian
(74) *Attorney, Agent, or Firm* — Purdue Research Foundation

(57) ABSTRACT

A formulation to deter abuse of a drug by smoking comprising a physical barrier having properties to entrap the drug and thermal degradation products thereof. The physical barrier is in the form of an additive or a polymer network or a combination thereof.

5 Claims, 12 Drawing Sheets

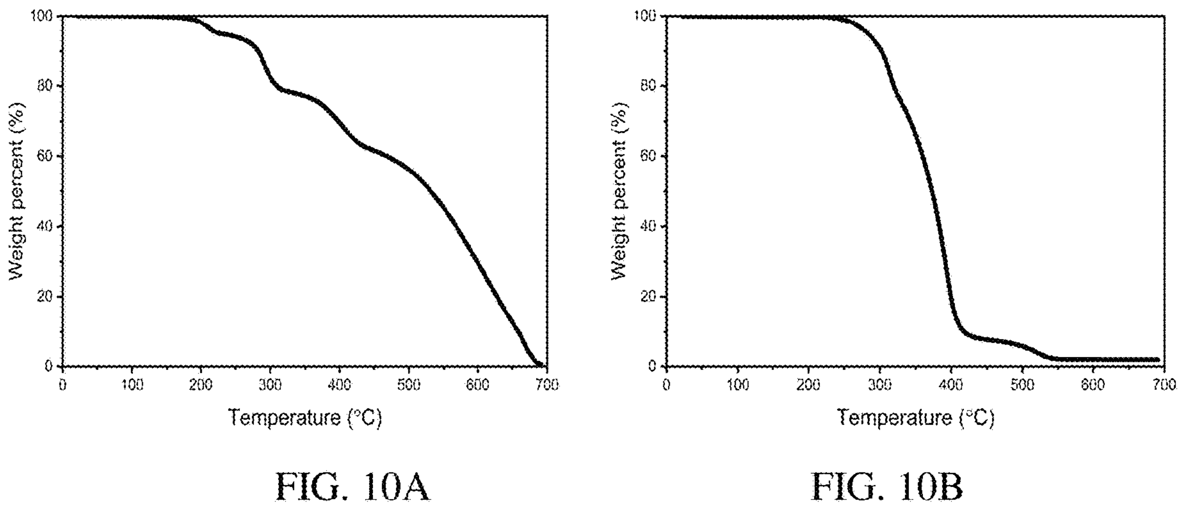
FIG. 10A
FIG. 10B
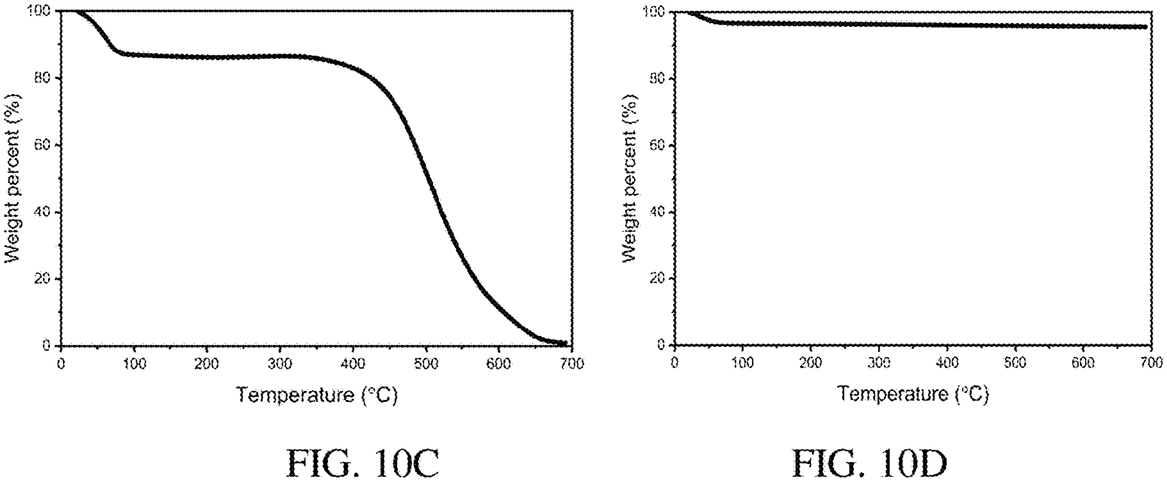
FIG. 10C
FIG. 10D

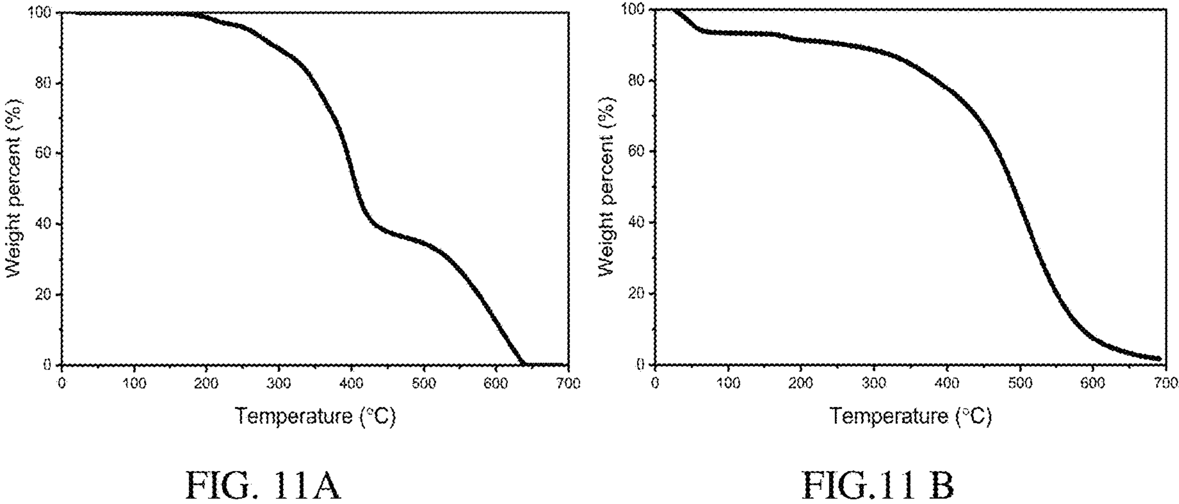
FIG. 11A
FIG.11 B
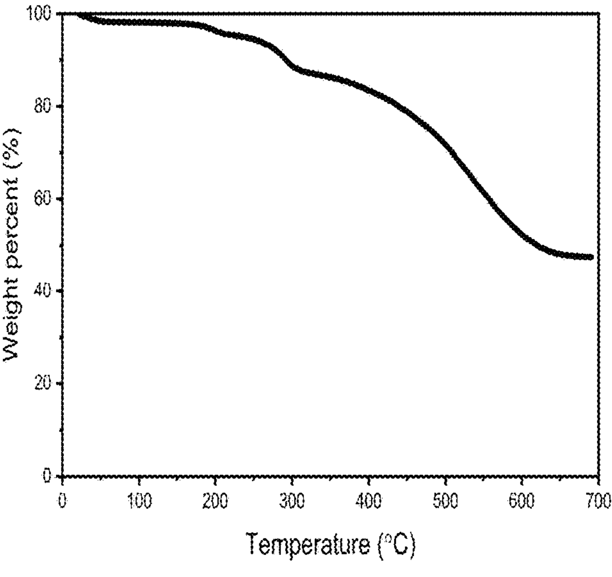
FIG. 11 C

FORMULATION TO DETER ABUSE OF DRUGS BY SMOKING

CROSS-REFERENCE TO RELATED APPLICATION

This application claims priority to U.S. provisional patent application No. 63/354,260, which was filed Jun. 22, 2022, and which is hereby incorporated by reference in its entirety.

GOVERNMENT RIGHTS

This invention was made with government support under contract number awarded by the National Institutes of Health. The government has certain rights in the invention.

TECHNICAL FIELD

Smoking provides a rapid and efficient method of drug delivery from the lungs to the brain, contributing to its abuse potential. The present disclosure relates to the field of abuse-deterrent formulations for prescription drugs, such as opioids, to prevent their abusive use by smoking.

BACKGROUND

Abuse of prescription drugs is a public health problem. The most common class of drug that is likely to be abused is opioids. Drugs like opioids are frequently prescribed across the country for pain relief, despite the alarming prevalence of their abuse, that often leads to addiction and overdose deaths. Prescription opioid abuse is a critical public health issue in the United States. Abuse is described as "any intentional, non-therapeutic use of a drug product or substance, even once, for the purpose of achieving a desirable psychological or physiological effect" (Smith et al., 2013, Pain, 154(11), 2287-2296).

The main routes of prescription opioid abuse are ingestion, injection, and inhalation, including insufflation and smoking. Alternate routes of administration typically require the addict to tamper physically with opioids (for example, by crushing or grinding) to convert them into a powder prior to alternate administration to achieve the desired effects more rapidly. Abuse deterrent formulations (ADFs) have been developed to decrease prescription opioid abuse while keeping these medications accessible to patients who need them. ADFs for prescription opioids are aimed at making non-medical use of these drugs more challenging, and less satisfying for abuse.

ADF technologies developed to date include physical/mechanical barriers, aversion approaches, agonist/antagonist combinations, and prodrugs (Schaeffer T., 2012, Journal of Medical Toxicology, 8(4), 400-407). Prescription opioid ADFs currently available on the market are designed to resist crushing, extraction of the full opioid dose from the pill, insufflation, injection, and oral abuse by chewing (Adler and Mallick-Searle, 2018, Journal of Multidisciplinary Healthcare, 11, 323-332). When compared to other common abuse methods like injection, smoking offers several advantages to addicts such as, for example, the ability to better control the high, reduction in social stigma due to diminished scarring caused by injections, and improved health outcomes owing to less tissue infections (Kral et al., 2021, Drug and Alcohol Dependence, 227, 109003). Abusers smoke opioids by placing them on aluminum foil, heating and then inhaling the emitted vapor through a tube (Kimergard et al., 2018, Drug Testing and Analysis, 10(6), 917-926). The drug contained in the vapor quickly enters the bloodstream through the lungs and immediately travels to the brain, causing an intense high (Kalant, 1997, Addiction, 92(3), 267-277). The other common method is called Ack. This method uses the heroin and opioids in a form resembling a cigarette so that it may look like the user is smoking a common nicotine cigarette.

Even though smoking is one of the most common methods of abusing prescription opioids, to date, no ADF currently exists to deter this particular route of abuse. Hence there is an unmet need for an approach to deter smoking of opioids, such as prescription drug opioids. Therefore, it is an object of the present disclosure to provide a formulation to deter abuse of a drug by smoking. This and other objects and advantages, as well as inventive features, will be apparent from the detailed description.

SUMMARY

Provided is a formulation to deter abuse of a drug by smoking. The formulation comprises a physical barrier, wherein the physical barrier is an additive or a polymer network or a combination thereof which entraps the drug and its thermal degradation products.

The physical barrier can be an additive or a polymer network. The physical barrier can be a combination of an additive and a polymer network. The physical barrier is selected from one or more polymers, a molecular sieve, a mesoporous silica, an activated carbon, or a combination thereof. In some embodiments, the additive is or comprises a molecular sieve, a mesoporous silica, an activated carbon, or a combination thereof.

The polymer network can be in the form of a microsphere (MS), a microcapsule, a bead, a nanoparticle, a nanotube, a nanorod, or a microdot. In an exemplary embodiment, the polymer network is in the form of a microsphere. The polymer network includes one or more polymers.

In some embodiments, the polymers are in the form of a polymer blend including two or more polymers. The polymers can be hydrophobic polymers or hydrophilic polymers, or a combination thereof. Desirably, the polymers are biocompatible and biodegradable.

In exemplary embodiments, the polymers include poly(lactides), poly(glycolides), poly(lactide-co-glycolides), poly(lactic acid)s, poly(glycolic acid)s, poly(lactic acid-co-glycolic acids)s, polycaprolactones, polycarbonates, polyesteramides, polyanhydrides, poly(amino acids), polyorthoesters, polycyanoacrylates, poly(p-dioxanone)s, poly(alkylene oxalate)s, poly (ethylene oxide), poly (ethylene glycol), poly (vinyl pyrrolidone), poly (vinyl alcohol), poly (acrylic acid), polyacrylamide, poly (isopropyl acrylamide), poly (cyclopropyl methacrylamide), polycyanoacrylate, poly (methyl acrylate), 2-ethylhexyl acrylate, poly (butyl acrylate), poly (methyl methacrylate), poly (hydroxyethyl methacrylate), polychloroprene, polyisobutylene, poly (vinyl acetate), ethylene vinyl acetate, polystyrene, polypropylene, poly (vinyl chloride), polyethylene, polyethylene terephthalate, silicones, biodegradable polyurethanes, cellulose and its derivatives (such as ethyl cellulose, carboxymethyl cellulose, hydroxyethyl cellulose, hydroxypropyl cellulose, hydroxypropyl methyl cellulose, and cellulose acetate phthalate), alginic acid, hyaluronic acid, pectinic acid, collagen, gelatin, starch, sodium starch glycolate, carrageenan, chitosan, and blends and copolymers thereof.

Provided is a microsphere formulation to deter abuse of a drug by smoking comprising a physical barrier, which includes a polymeric blend of two or more polymers that entrap the drug and its thermal degradation products.

In some embodiments, the two or more polymers used in the formulation are polylactic acid (PLA) and polycaprolactone (PCL). PLA and PCL are in a ratio ranging from 1:9 to 9:1. Particularly, PLA and PCL are in the ratio of 1:9, 5:5, or 9:1.

The diameter of PLA-PCL microspheres (PLA-PCL MS) is smaller than the diameter of human capillaries (5 μm), which makes them safe to use in patients. The average diameter of the microsphere ranges from about 1.5 μm to about 4.0 μm.

Examples of the drug that can be abused include, but are not limited to, opioids, sedatives, central nervous system (CNS) depressants, CNS stimulants, and hallucinogens. In an exemplary embodiment, the drug is an opioid.

Provided is a method of deterring abuse of an oral dosage form of a drug, which can be abused by smoking, which method comprises incorporating into the oral dosage form of the drug a formulation of the disclosure, which entraps the drug and thermal degradation products thereof, whereupon the oral dosage form of the drug deters abuse.

BRIEF DESCRIPTION OF THE DRAWINGS

The present invention will be more readily understood from the detailed description of embodiments presented below considered in conjunction with the attached drawings of which:

FIG. 10A illustrates TGA weight loss curves of THB obtained at a 20° C./min heating rate in air.

FIG. 10B illustrates TGA weight loss curves of PLA-PCL MS, in which PLA and PCL are in a molar ratio of 1:9 obtained at a 20° C./min heating rate in air.

FIG. 10C illustrates TGA weight loss curves of AC obtained at a 20° C./min heating rate in air.

FIG. 10D illustrates TGA weight loss curves of MPS obtained at a 20° C./min heating rate in air.

FIG. 11A illustrates TGA weight loss curves of a THB+PLA-PCL MS mixture (1:1 by mass) obtained at a 20° C./min heating rate in air.

FIG. 11B illustrates TGA weight loss curves of THB+AC mixture (1:1 by mass) obtained at a 20° C./min heating rate in air.

FIG. 11C illustrates TGA weight loss curves of THB+MPS mixture (1:1 by mass) obtained at a 20° C./min heating rate in air.

Figure 1:
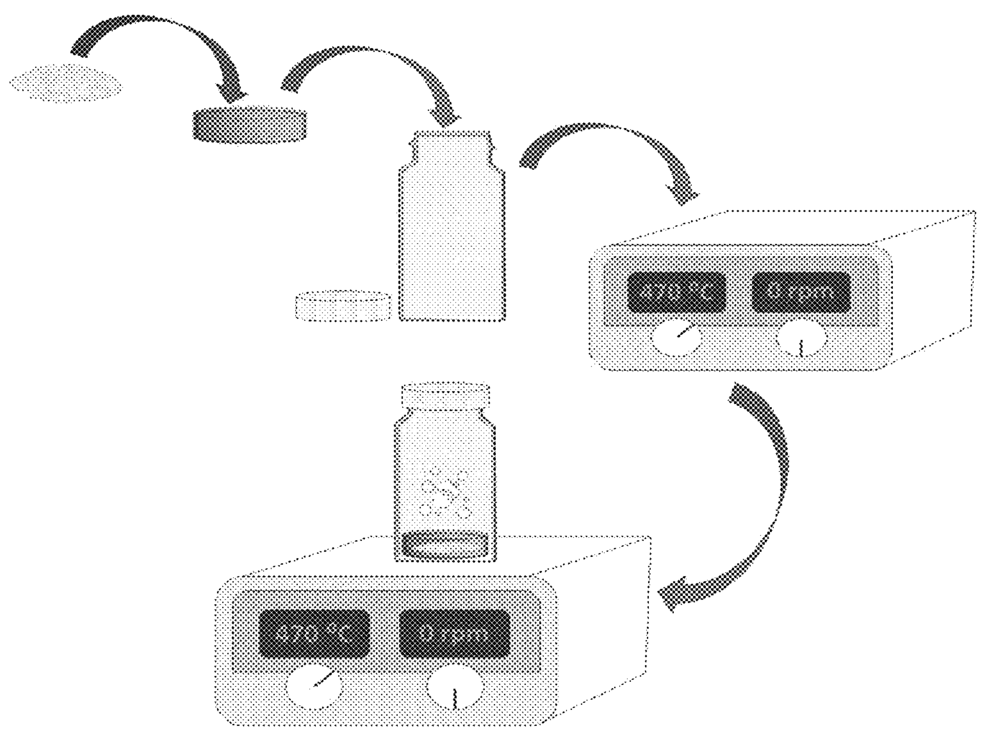
FIG. 1 illustrates the setup used to vaporize an opioid drug (Thebaine (THB)) in a laboratory setting. THB was added to a weighing dish, which was placed inside a scintillation glass vial (20 ml). The glass vial was placed on a pre-heated hotplate to a setpoint of 470±° C. The vial was kept on the hotplate for 1 minute to allow THB to vaporize.

It is to be understood that the attached drawings are for the purposes of illustrating the concepts of the invention and may not be to scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the claimed invention is thereby intended.

The term "about" can allow for a degree of variability in a value or range, for example, within 10%, within 5%, or within 1% of a stated value or of a stated limit of a range.

The term "substantially" can allow for a degree of variability in a value or range, for example, within 90%, within 95%, or within 99% of a stated value or of a stated limit of a range.

The terms "a," "an," or "the" are used to include one or more than one unless the context clearly dictates otherwise. The term "or" is used to refer to a nonexclusive "or" unless otherwise indicated. In addition, the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. The terms "including" and "having", are defined as comprising (i.e., open language).

The term "drug" refers to a pharmaceutically active ingredient, which is incorporated into a formulation.

The term "polymer" refers to molecules made up of monomers (e.g., repeating units linked together). "Polymers" are understood to include, but are not limited to, homopolymers, copolymers, such as for example, block, graft, random and alternating copolymers, terpolymers, etc. and blends and modifications thereof. "A polymer" can be a three-dimensional network (e.g., the repeating units are linked together left and right, front and back, up and down), a two-dimensional network (e.g., the repeating units are linked together left, right, up, and down in a sheet form), or a one-dimensional network (e.g., the repeating units are linked left and right to form a chain). "Polymers" can be composed of natural monomers, synthetic monomers, or combinations thereof. The polymers can be biologic (e.g., the monomers are biologically important (e.g., an amino acid), natural, or synthetic.

The term "entrap" refers to the prevention of a drug from going into vapor phase.

Smoking route of drug administration and drug formulation determines the rate of drug absorption. Smoking provides a rapid and efficient method of drug delivery from the lungs to the brain, contributing to its abuse potential.

In an embodiment, provided is a formulation to deter abuse of a drug by smoking comprising a physical barrier, wherein the physical barrier is an additive or a polymer network or a combination thereof which entraps the drug and its thermal degradation products.

Example of the drugs that can be abused include, but are not limited to, opioid drugs, sedatives, central nervous system (CNS) depressants, CNS stimulants, and hallucinogens. Opioid drugs include, but are not limited to, oxycodone, hydrocodone, morphine, methadone, meperidine, thebaine, tramadol, and fentanyl, and are commonly prescribed drugs to relieve pain.

The physical barrier entraps physically the drug. It minimizes the abuse potential of the drug by reducing the amount of drug, or preventing the drug, from going into the vapor phase when consumed by smoking and, therefore, reduces the amount of the abusive drug available, so that little or no high is achieved. The selected physical barrier is stable, non-toxic with no toxic by-products, and does not get mixed into the drug vapors during smoking. It can affect the partitioning of the drug or have an affinity for the drug that prevents the drug from going into vapor phase.

The physical barrier can be an additive or a polymer network. The physical barrier can be a combination of the additive and polymer network. In various embodiments, the additive is or comprises a molecular sieve, a mesoporous silica, an activated carbon, or a combination thereof. In some embodiments, the physical barrier is in the form of a polymer network. The polymer network can be a single polymer or a combination of two or more polymers in network form. The polymer network can prevent drug aerosol formation.

The polymer network can be in the form of a microsphere (MS), a microcapsule, a bead, a nanoparticle, a nanotube, or a nanorod. In some embodiments, the polymer network is in the form of a microsphere.

The microsphere formulation offers porosity, specific surface area, and/or intermolecular interactions that help prevent a drug going from vapor phase via smoking route to human system. The diameter of microsphere particles can range from about 100 nm to about 500 μm, such as from 100 nm to about 500 μm or about 100 nm to 500 μm.

In various embodiments, a microsphere formulation comprises a physical barrier, wherein the physical barrier includes one or more polymers, molecular sieve, mesoporous silica, activated carbon, or a combination thereof.

Further, provided is a microsphere formulation to deter abuse of the drug by smoking. The formulation comprises a polymer blend, which comprises one or more polymers and acts as a physical barrier. This polymeric blend formulation functions as a sink for the active drug and degradation products thereof. As an example, the polymers that can be used are one or more biocompatible and biodegradable polymers. The polymers can be hydrophobic polymers or hydrophilic polymers, or any combination thereof.

In some embodiments, the polymers are selected from the group comprising of poly(lactides), poly(glycolides), poly (lacticle-co-glycolides), poly(lactic acid)s, poly(glycolic acid)s, poly(lactic acid-co-glycolic acids)s, polycaprolactones, polycarbonates, polyesteramides, polyanhydrides, poly(amino acids), polyorthoesters, polycyanoacrylates, poly(p-dioxanone)s, poly(alkylene oxalate)s, poly(ethylene oxide), poly(ethylene glycol), poly(vinyl pyrrolidone), poly (vinyl alcohol), poly(acrylic acid), polyacrylamide, poly (isopropyl acrylamide), poly(cyclopropyl methacrylamide), polycyanoacrylate, poly(methyl acrylate), 2-ethylhexyl acrylate, poly(butyl acrylate), poly(methyl methacrylate), poly(hydroxyethyl methacrylate), polychloroprene, polyisobutylene, poly(vinyl acetate), ethylene vinyl acetate, polystyrene, polypropylene, poly (vinyl chloride), polyethylene, polyethylene terephthalate, silicones, biodegradable polyurethanes, cellulose and its derivatives (such as ethyl cellulose, carboxymethyl cellulose, hydroxyethyl cellulose, hydroxypropyl cellulose, hydroxypropyl methyl cellulose, and cellulose acetate phthalate), alginic acid, hyaluronic acid, pectinic acid, collagen, gelatin, starch, sodium starch glycolate, carrageenan, chitosan, and blends and copolymers thereof.

In some embodiment, the biocompatible and biodegradable polymers that are used to make the formulation are polylactic acid (PLA) and polycaprolactone (PCL).

The polymers are selected based on their discrete thermal properties. The selected polymers that can undergo melting transitions at temperatures lower than the boiling point of most drugs, which can be abused, and form the liquified polymer matrix to facilitate the entrapment of vapors of the drug. Melting temperature of PLA is higher than that of PCL. PLA and PCL undergo melting transitions that onset at around 160° C. and 52° C., respectively. PLA melts faster and combines with the melting of PCL, which helps entrap the viable drug without simultaneously degrading. This polymer blend is effective for drug entrapment. Both PLA and PCL begin thermally decomposing at a higher temperature than the drug, so the polymers are fully functional within the temperature range in which the drug is active. When the microsphere PLA-PCL formulation is physically mixed with the drug and heated beyond the melting point of the PLA-PCL microsphere, the microspheres liquefy, and the molten polymer blend prevents the drug from escaping into the vapor, thereby reducing the amount of the drug that enters the vapor phase.

The polymer blend of two or more polymers provides the best results. PLA and PCL are combined in various ratio. In an embodiment, PLA and PCL are combined in the ratio range from about 1:9 to about 9:1, such as about 1:9 to 9:1 or 1:9 to about 9:1. The effective ratios of PLA and PCL are about 1:9, such as 1:9, about 5:5, such as 5:5, or about 9:1, such as 9:1. The greatest reduction of the amount of the active drug going into vapor is achieved when the ratio of PLA and PCL is about 1:9, such as 1:9.

The combination of polymers or polymer blend of PCA and PCL provides small diameter and rough, wrinkled surfaces and hence effectively reduces the amount of the active drug going into vapor. The diameter of PLA-PCL microspheres (PLA-PCL MS) is smaller than the diameter of human capillaries (5 μm), which makes them safe to use in patients.

In some embodiments, the average diameter of PLA-PCL MS particles ranges from about 1.5 μm to about 4.0 μm, such as about 1.5 μm to 4.0 μm or 1.5 μm to about 4.0 μm. The average diameter PLA-PCL MS particles ranges from about 1.5 μm to about 3.5 μm, such as about 1.5 μm to 3.5 μm or 1.5 μm to about 3.5 μm.

Microspheres are formulated with a variety of known methods. As an example, the MS formulation of PLA-PCL is prepared by a single emulsion-solvent evaporation method, followed by freeze-drying. In an embodiment, the MS formulation of PLA-PCL is prepared by a single emulsion-solvent evaporation method, followed by freeze-drying, wherein PLA and PCL are combined in various ratio ranging from about 1:9 to about 9:1, such as about 1:9 to 9:1 or 1:9 to about 9:1.

The drug used to demonstrate the drug-entrapment capacity of the MS formulation of PLA-PCL is an opioid drug. The opioid drug is Thebaine (THB). Melting temperatures of PLA-PCL (~160° C. and ~52° C., respectively) are well below the boiling point of THB (~468° C.). Additionally, PLA and PCL have high thermal decomposition temperatures, such as about 237° C. and about 319° C., respectively, well below the thermal decomposition temperature of about 183° C. of THB.

The drug entrapment capacity of PLA-PCL MS formulations with varying ratios of PLA to PCL were tested by doing various analytical tests. The varying ratios of PLA to PCL were 1:9, 5:5, and 9:1. Scanning electron microscopy (SEM) was utilized to determine the average particle diameters. The thermal properties of PLA, PCL, and PLA-PCL MS were obtained using differential scanning calorimetry (DSC) and thermogravimetric analysis (TGA) to demonstrate that the thermal profiles of the selected polymers were suitable for formulation. Drug vaporization studies, high-performance liquid chromatography (HPLC), and TGA were used to analyze the entrapment of THB by the polymer blend microparticles in comparison to the positive controls, namely activated carbon (AC) and mesoporous silica (MPS). MPS is commonly used in heavy metal adsorption to form aqueous solutions and can be formulated with different pores, which are sized to maximize adsorption, and AC is used in the adsorption of gases, such as carbon dioxide and oxygen.

DSC data showed that PLA and PCL soften and eventually liquefy at temperatures significantly lower than the boiling point of THB. Thermal stability of PLA and PCL was determined using TGA to demonstrate that the polymers begin thermally breaking down at higher temperatures than the drug. DSC data also indicated that, by changing the polymer ratios in the formulations, the melting behavior of the particles can be manipulated.

TGA data confirmed that PLA-PCL MS indeed have blended thermal properties. TGA analysis showed that there is a significant drop in the loss of mass when the PLA-PCL microspheres are used with THB. This resulted in about a 14.5% decrease in mass loss, supporting the entrapment of the viable drug.

HPLC and TGA were performed to test the ability of PLA-PCL MS to limit the escape of vaporized THB. THB was heated alone, and THB was mixed with PLA-PCL MS to the drug's predicted boiling point ~468° C. The samples were heated to 470° C. (to account for 2° C. oscillations of the hotplate temperature around the setpoint), the emitted vapor was collected and the amount of active drug in the vapor was quantified using HPLC. It was found that PLA-PCL MS significantly lowered the percentage of active THB in the vapor compared to THB alone. The best results were obtained wherein the molar ratio of PLA to PCL was 1:9. According to the total area under the curve (AUC) per mg of THB, which indicates the total amount of vaporized THB and its degradation products, PLA-PCL MS, in which the molar ratio of PLA to PCL was 1:9, significantly reduced the amount of thermal degradation products of THB in the vapor compared to THB alone.

Additionally, the abuse-deterrent potential of PLA-PCL MS was compared to that of AC and MPS, two materials with excellent drug-adsorbing properties. However, AC and MPS are comparatively less suitable for ADF. AC is a strong adsorbent that can reduce the therapeutic efficacy of prescription opioids, while the use of MPS has safety concerns associated with it. It has been observed that the MS formulation effectively reduced the amount of both active drug and thermal degradation products of THB in the smoke. PLA-PCL MS was comparable to MPS in terms of the abuse-deterrent performance. The advantage of the PLA-PCL MS formulation is that it does not affect the therapeutic efficacy of the drug if taken as a regularly prescribed drug.

Thus, the vaporization studies and TGA data indicate that non-polar thermal degradation products of THB formed when the drug is heated beyond 200° C. have a high affinity for the hydrophobic molten polymer matrix and are readily trapped by it. These captured thermal decomposition products form a hydrophobic layer that prevents the active drug from going into the vapor when THB reaches its predicted boiling temperature, at which point both PLA and PCL are also fully thermally degraded.

PLA-PCL MS in which PLA and PCL are in the molar ratio of 1:9 can serve as a safe and effective method to reduce the smoking efficiency of prescription opioids, as shown on THB. The MS formulation of PLA-PCL acts as a physical barrier that helps significantly decrease the amount of active drug and its potentially harmful thermal decomposition products in the vapor released when the drug is heated. The drug-entrapment capacity of MS is comparable to that of MPS, a material known for its excellent drug-adsorbing properties.

The formulation can be used to form a nano- or microparticle-based drug delivery system that can be administered via extraction, injection, and insufflation routes for deterrence of prescription opioid abuse by smoking. Also, the formulation can be integrated with the existing microparticle drug formulations for opioids.

Provided is a formulation to combine with a drug to deter abuse of the drug by smoking, which formulation comprises microspheres, which comprise polylactic acid and polycaprolactone in a ratio ranging from about 1:9 to about 9:1, wherein the microspheres have an average diameter from about 1.5 μm to about 4.0 μm.

Further, provided is a formulation to deter abuse of a drug, which can be abused by smoking, which formulation comprises (i) the drug and (ii) a physical barrier, which entraps the drug and thermal degradation products thereof.

Provided is a method of deterring abuse of an oral dosage form of a drug, which can be abused by smoking, which method comprises incorporating into the oral dosage form of the drug a formulation of the disclosure, which entraps the drug and thermal degradation products thereof, whereupon the oral dosage form of the drug deters abuse.

Provided is a method of deterring abuse of an oral dosage form of a drug, which can be abused by smoking, which method comprises incorporating into the oral dosage form of the drug a formulation, which formulation comprises microspheres, which comprises polylactic acid and polycaprolactone which entraps the drug and thermal degradation products thereof.

Polylactic acid and polycaprolactone microspheres can be co-formulated in a tablet with a drug, which can be abused, to deter its abuse via the smoking route.

With various embodiments have been described, it will be apparent to those of ordinary skill in the art that many more embodiments and implementations are possible. Accordingly, the embodiments described herein are examples, not the only possible embodiments and implementations.

EXPERIMENTAL

The Chemicals are Procured from:

THB from Sigma-Aldrich, Dichloromethane from Sigma-Aldrich, PLA (acid endcap, Mn 100,000-125,000 Da) and PCL (acid endcap, Mn 75,000-85,000 Da) from PolySciTech, Polyacrylic acid (average Mv~1,250,000) from Sigma-Aldrich and Hotplate—Thermo Scientific All data are reported as mean±standard deviation. The statistical analyses were performed using Minitab software (Minitab Inc., State College, PA, USA). The Tukey test was used to obtain multiple pairwise comparisons between experimental groups.

PLA-PCL Microspheres

PLA-PCL MS with varying molar ratios of PLA to PCL were prepared using a single emulsion-solvent evaporation method.

Dichloromethane (2 ml) were added to a scintillation glass vial (20 ml) containing a total of 200 mg of PLA (acid endcap, Mn 100,000-125,000 Da) and PCL (acid endcap, Mn 75,000-85,000 Da). The mixture was stirred on a magnetic hotplate for 20 minutes at 150 rpm until the polymers fully dissolved. The organic phase was then transferred to a scintillation glass vial (20 ml) containing 0.1% (w/v) solution of polyacrylic acid (18 ml) (average Mv~1,250,000) in MilliQ water. The vial was placed in an ice bath, and the solution was then sonicated for 30 minutes at a 40% amplitude. Next, the solution was transferred to a glass beaker containing MilliQ water (95 ml) and stirred for 2 hours at 200 rpm. The resulting PLA-PCL MS were centrifuged and washed with MilliQ water twice. The particles were then freeze-dried for 48 hours. The lyophilized microspheres were stored at ~20° C. until further use. The PLA-PCL MS are characterized by following analytical methods.

Analytical Data

1. Scanning Electron Microscopy

The images were acquired on a FEI Nova nanoSEM field emission scanning electron microscope (FEI Company, Hillsboro, OR) using Everhart Thornley detector (ETD). The settings used for image acquisition were: 5000× magnification, a 5.0±0.3 mm working distance, 5.00 kV accelerating voltage and 3.0 spot size. Prior to imaging, the samples were coated with platinum in a Cressington 208HR sputter coater. The images were analysed using ImageJ software to obtain particle diameters.

2. Differential Scanning Calorimetry

Samples of 1.4-8.8 mg were weighed in Tzero aluminum pans (TA Instruments, New Castle, DE). The pans were sealed using Tzero aluminium lids (TA Instruments, New Castle, DE). The experiments were performed on a Q2000 differential scanning calorimeter (TA Instruments, New Castle, DE) equipped with the liquid nitrogen cooling system (LNCS). The nitrogen purge flow rate was set to 50 ml/min. Each sample was subjected to a customized heating-cooling-heating test, with a heating/cooling rate of 20° C./min. All experiments were conducted in triplicate (n=3). The data were exported, and the second heating curves were analysed using TA Universal Analysis Software (Universal Analysis 2000 Version 4.5A, TA Instruments-Waters LLC, New Castle, DE). The software was used to determine glass transition onset temperatures ($T_{on,glass}$), inflection point temperatures ($T_{i,glass}$) and end temperatures ($T_{end,glass}$) of the individual polymers, as well as their melting onset temperatures ($T_{on,melting}$) and peak maximum temperatures ($T_{max,melting}$). The values were averaged and reported as mean±standard deviation.

3. Drug Vaporization Study

FIG. 1 shows the setup used for drug vaporization study of an opioid drug (Thebaine (THB)) in a laboratory setting. To measure the mass of vaporized drug under controlled conditions that mimic the process of opioid smoking, first, 5±0.5 mg of THB was placed inside a micro aluminum weighing dish (13 mm Dia.×3.5 mm H, 0.35 mL, Cole-Parmer) and spread in a thin layer. The dish was then carefully placed inside a 20 ml scintillation glass vial (insert manufacturer). The vial was capped and placed on a hotplate (Thermo Fisher Scientific) pre-equilibrated at a setpoint of 470±2° C. for 1 minute. Then, the vial was removed from the hotplate and allowed to cool down for 30 minutes. Next, the vial was uncapped, the dish was removed, and 8 ml of 0.1 M hydrochloric acid (HCl) was added. The vial was then capped, wrapped in aluminum foil, and placed on the Labquake shaker for 2 hours to elute the drug from the vapor that had condensed inside the vessel. To evaluate the ability of the MS to function as an opioid scavenging agent, we repeated the process with an equivalent mixture of 5±0.5 mg of thebaine and an equal mass of MS. Mesoporous silica (MPS) (2 um particle sizer with a 4 nm pore size, Sigma Aldrich) and activated carbon powder (AC) (ash 4% max, Alfa Aesar) are molecular sieves that were used as a positive control for scavenging thebaine. Vaporization experiments were replicated 5 times (n=5) for each treatment condition.

4. High-Performance Liquid Chromatography

A reverse phase HPLC system with an Ascentis $C_{18}$ analytical column (250 mm×4.6 mm, particle size 5 μm) (Supelco, St. Luis, MO, USA; 1100 series, Agilent Technologies, Palo Alto, CA, USA). The mixture of 30% acetonitrile (ACN) and 70% MilliQ water was used as a mobile phase. The mobile phase flow rate was set to 1 ml/min, the UV detector wavelength—to 285 nm, and the injection volume—to 25 μL. To prepare the samples from the drug vaporization study for HPLC analysis, 1.5 ml of each sample were aliquoted into individual 2 ml microcentrifuge tubes and centrifuged for 12 minutes at 13.2 rpm. Then, 1 ml of supernatant was removed from each tube using a syringe and passed through a syringe filter (0.2 μm pore size) into HPLC vials. A wash sample with the same composition as the mobile phase was prepared and filtered as well. The data collected for each of the samples were compiled. Total active drug concentration, percentage of active drug vaporized, and the total area under the curve per milligram (mg) of THB were calculated. One-way ANOVA and Tukey pairwise comparisons were used for statistical analysis.

5. Thermogravimetric Analysis

Samples of 8.0-18.2 mg were placed in platinum TGA sample pans (CS Ceramic) and heated from room temperature to 700° C. at 20° C./min in a furnace under either inert (nitrogen) or oxidizing (air) atmosphere. The experiments were performed in triplicates (n=3) or quintuplicates (n=5). The data were exported and the TGA curves were analysed using TA Universal Analysis Software (Universal Analysis 2000 Version 4.5A, TA Instruments-Waters LLC, New Castle, DE) to determine onset degradation temperatures ($T_{on,degradation}$) and weight percent losses of the materials used in this study over the temperature intervals of interest. The values were averaged and reported as mean±standard deviation.

Results

1. Characterization of PLA and PCL by Thermal Analysis

Figure 2A:
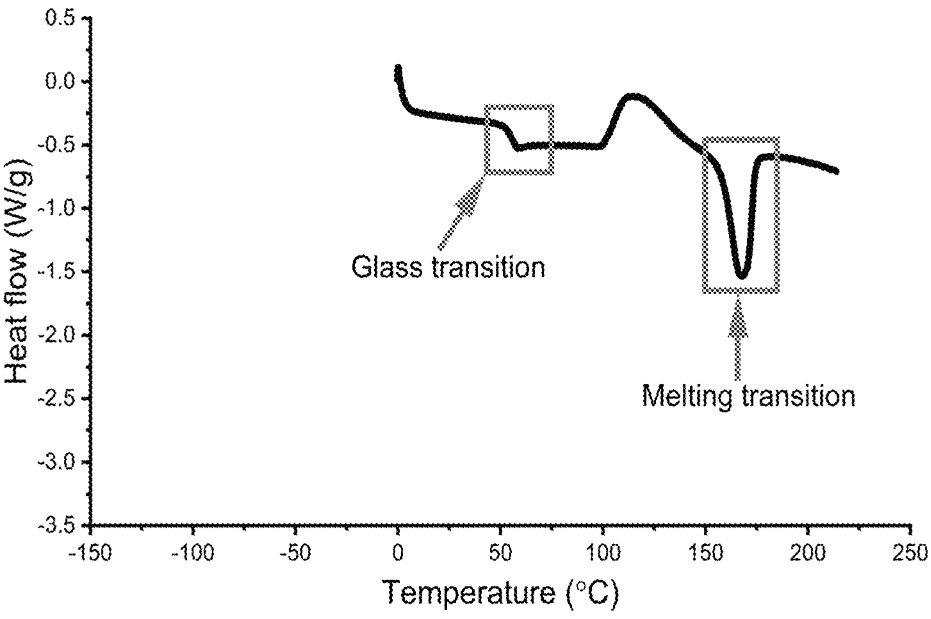
FIG. 2A illustrates a second heating differential scanning calorimetry (DSC) curve of polylactic acid (PLA) obtained at a 20° C./min heating rate.
Figure 2B:
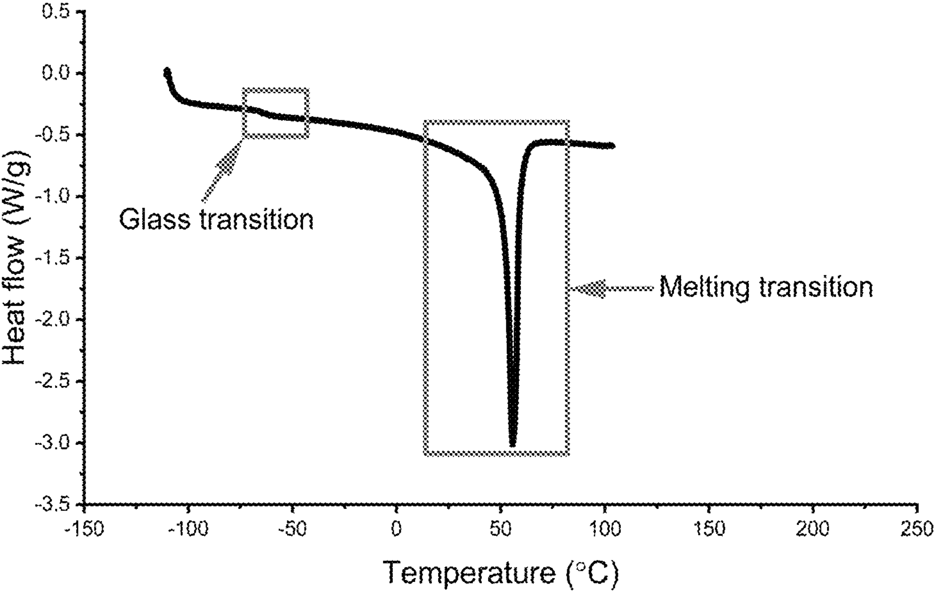
FIG. 2B illustrates a second heating DSC curve of polycaprolactone (PCL) obtained at a ° C./min heating rate.

DSC studies were carried out to characterize glass and melting transitions of PLA and PCL in order to show that they occurred below the vaporization temperature of the drug, allowing for formation of the liquefied polymer matrix facilitating THB entrapment. FIG. 2A and FIG. 2B show representative second heating DSC curves of PLA and PCL respectively. The mean values of $T_{on,glass}$, $T_{i,glass}$, $T_{end,glass}$, $T_{on,melting}$ and $T_{max,melting}$ (n=3) for PLA and PCL, as determined by DSC, are summarized in Table 1.

TABLE 1

| | PLA | PCL |
|---|---|---|
| $T_{on, glass}$ | 53.4 ± 0.9° C. | −66.7 ± 1.0° C. |
| $T_{i, glass}$ | 56.8 ± 0.5° C. | −63.5 ± 1.1° C. |
| $T_{end, glass}$ | 58.1 ± 0.8° C. | −60.6 ± 2.1° C. |
| $T_{on, melting}$ | 160.2 ± 1.3° C. | 168.4 ± 0.6° C. |
| $T_{max, melting}$ | 51.8 ± 0.6° C. | 56.0 ± 0.4° C. |

DSC data showed that both PLA and PCL soften and eventually liquefy at temperatures significantly lower than the boiling point of THB.

Figure 3A:
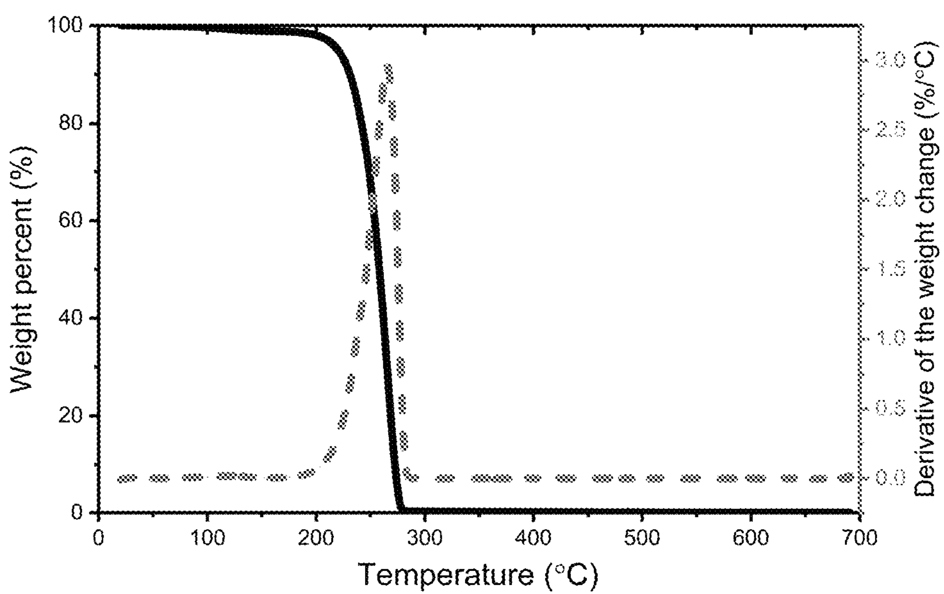
FIG. 3A illustrates thermogravimetric analysis (TGA) weight loss curves (solid lines) and derivative of the weight loss curves (dashed lines) of PLA obtained at a 20° C./min heating rate under nitrogen atmosphere.
Figure 3B:
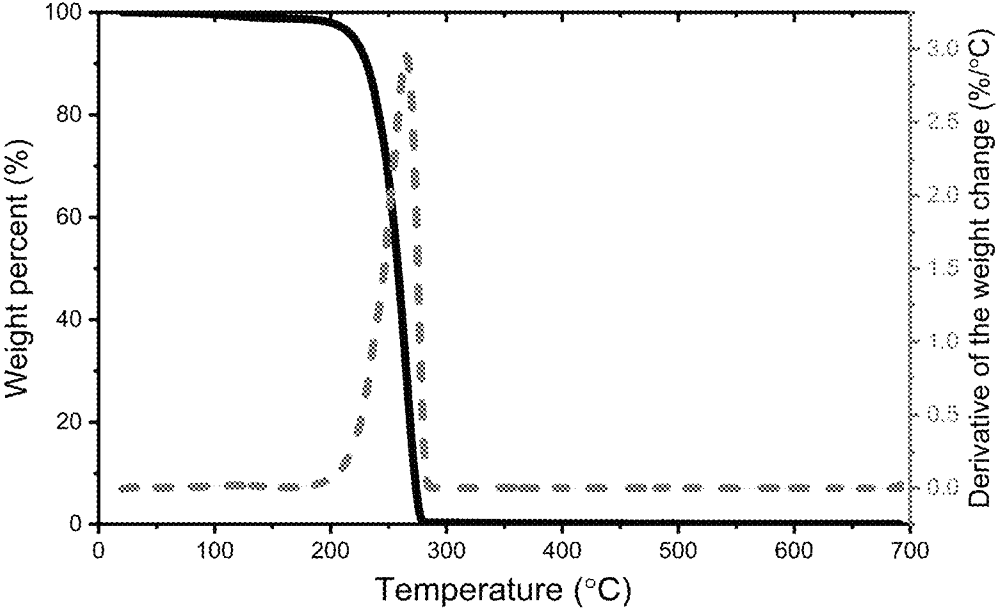
FIG. 3B illustrates TGA weight loss curves (solid lines) and derivative of the weight loss curves (dashed lines) of PCL obtained at a 20° C./min heating rate under nitrogen atmosphere.

Thermal stability of PLA and PCL was determined using TGA to demonstrate that the polymers begin thermally breaking down at higher temperatures than the drug. FIG. 3A and FIG. 3B show the TGA profiles for PLA and PCL respectively. The weight loss curves (solid lines) showed that both PLA and PCL underwent single-step decompositions. This was supported by the derivative curves (dashed lines), both of which displayed single peaks. The mean $T_{on,degradation}$ of PLA was 278.8±3.8° C., with the average weight percent loss of 98.6±0.3% (n=3) during the decomposition step. The mean $T_{on,degradation}$ of PCL was 353.1±1.7° C., and the weight percent loss averaged 97.9±1.1% (n=3).

1. Comparison of Polymer Blend Microsphere Formulations

Figure 4A:
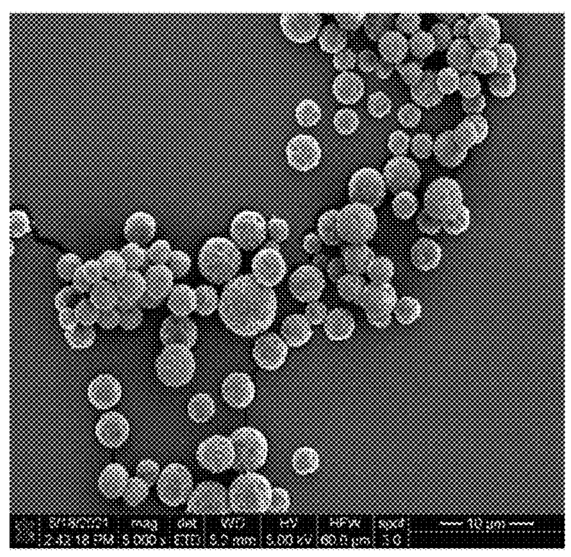
FIG. 4A illustrates scanning electron microscope (SEM) images of PLA-PCL microspheres (MS), in which PLA and PCL are in a molar ratio of 1:9, obtained at 5,000× magnification. Scale bar=10 μm.
Figure 4B:
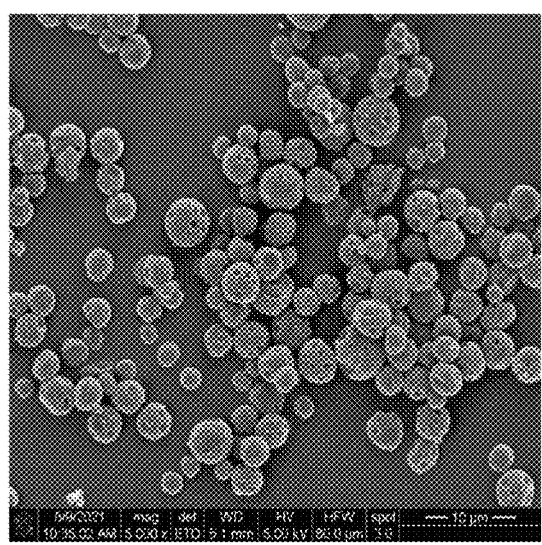
FIG. 4B illustrates SEM images of PLA-PCL MS, in which PLA and PCL are in a molar ratio of 5:5, obtained at 5,000× magnification. Scale bar=10 μm.
Figure 4C:
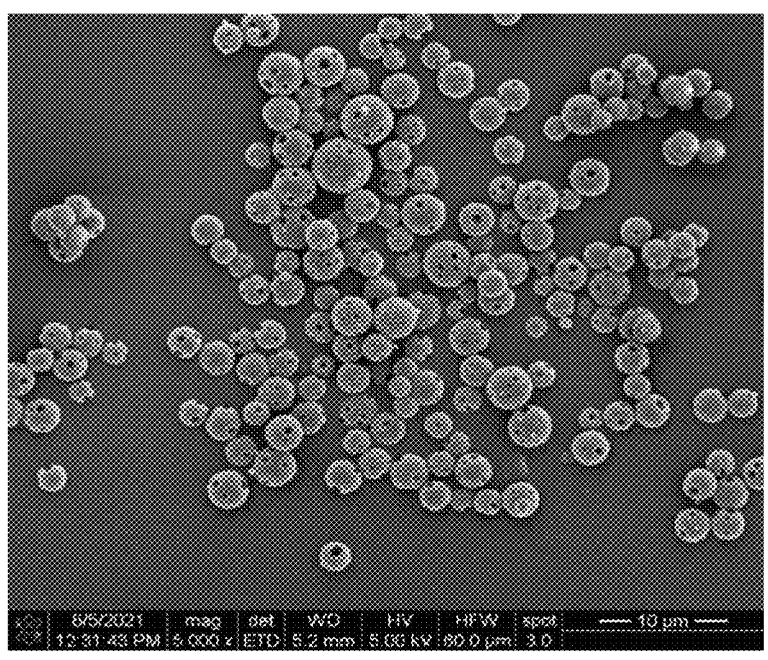
FIG. 4C illustrates SEM images of PLA-PCL MS, in which PLA and PCL are in a molar ratio of 9:1, obtained at 5,000× magnification. Scale bar=10 μm.

To select the particles with the best drug-entrapping capabilities, three different PLA-PCL MS formulations were prepared with varying molar ratios of PLA to PCL (1:9, 5:5 and 9:1). SEM and image analysis were utilized to obtain the particle size distributions for the three formulations. It was important to show that the MS diameters were smaller than the diameters of human capillaries (5-10 μm) to establish their safety for use in patients. The representative SEM images of the particles are shown in FIG. 4. The mean diameter of PLA-PCL MS (1:9) was 3.1±0.7 (n=1152 particles). The MS prepared using a 5:5 ratio of PLA to PCL had an average diameter of 2.4±0.7 (n=1641 particles), while the mean particle diameter for the 9:1 formulation was 2.3±0.5 (n=2745 particles).

Figure 5A:
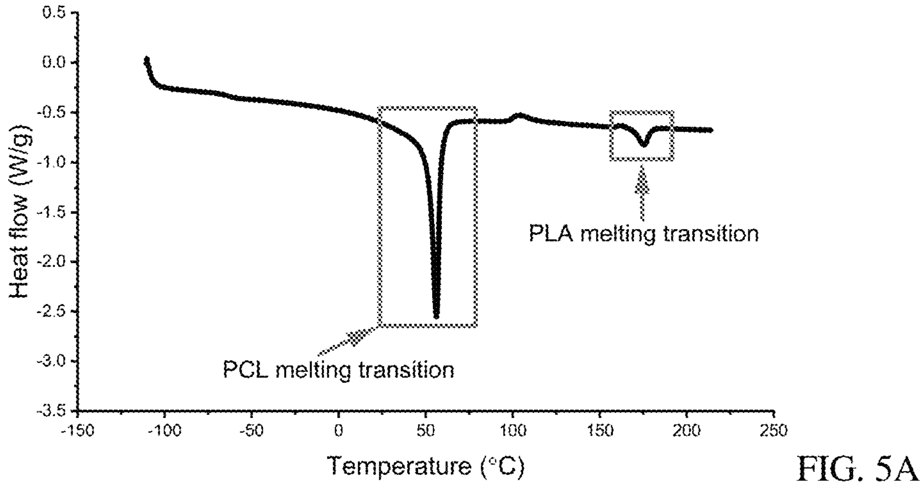
FIG. 5A illustrates second heating DSC curve of PLA-PCL MS, in which PLA and PCL are in a molar ratio of 1:9, obtained at a 20° C./min heating rate.
Figure 5B:
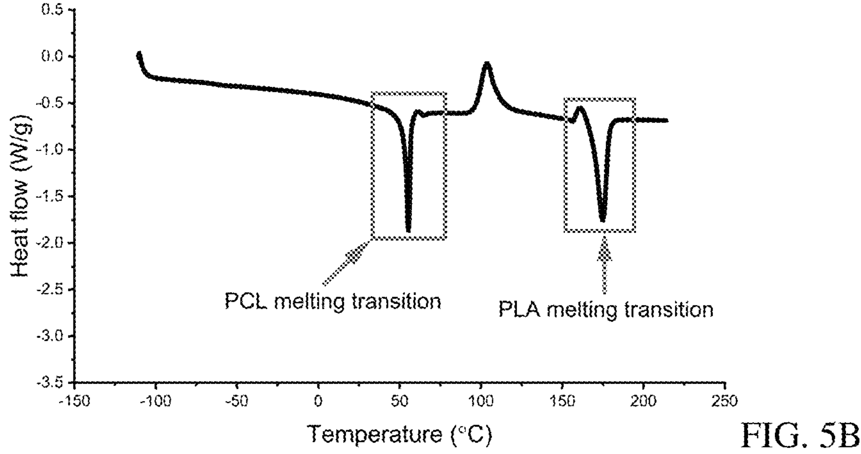
FIG. 5B illustrates second heating DSC curve of PLA-PCL MS, in which PLA and PCL are in a molar ratio of 5:5, obtained at a 20° C./min heating rate.
Figure 5C:
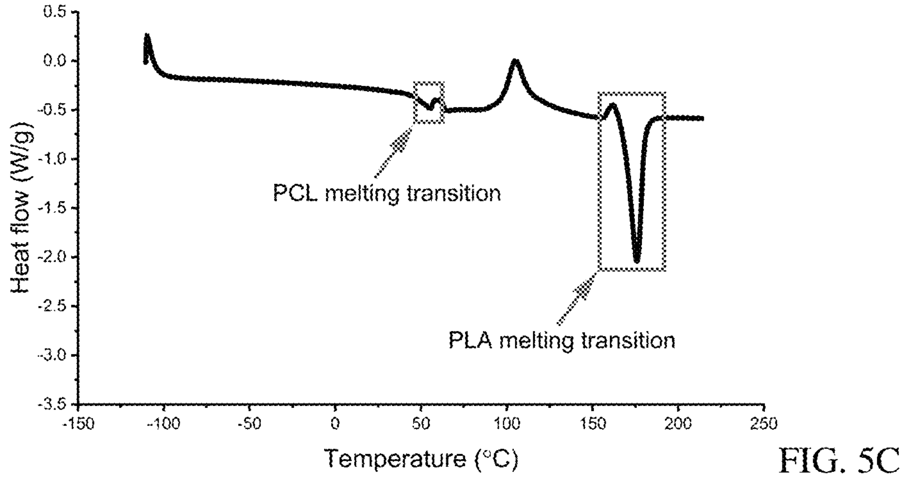
FIG. 5C illustrates second heating DSC curve of PLA-PCL MS, in which PLA and PCL are in a molar ratio of 9:1, obtained at a 20° C./min heating rate.

FIG. 5A-FIG. 5C shows representative second heating DSC curves for the three types of MS. All DSC graphs displayed two distinct melting transitions. The mean values of onset and peak maximum temperatures of these transitions (n=3) are summarized in Table 2.

TABLE 2

| | PLA-PCL MS (1:9) | PLA-PCL MS (5:5) | PLA-PCL MS (9:1) |
|---|---|---|---|
| $T_{on, melting}$ | 52.0 ± 0.1° C. and 169.4 ± 0.6° C. | 52.8 ± 0.2° C. and 168.7 ± 0.5° C. | 48.5 ± 2.0° C. and 168.1 ± 0.3° C. |
| $T_{max, melting}$ | 52.0 ± 0.1° C. and 175.1 ± 0.5° C. | 55.6 ± 0.2° C. and 175.2 ± 0.5° C. | 54.8 ± 0.1° C. and 175.7 ± 0.6° C. |

Figures 6A, 6B, 6C:
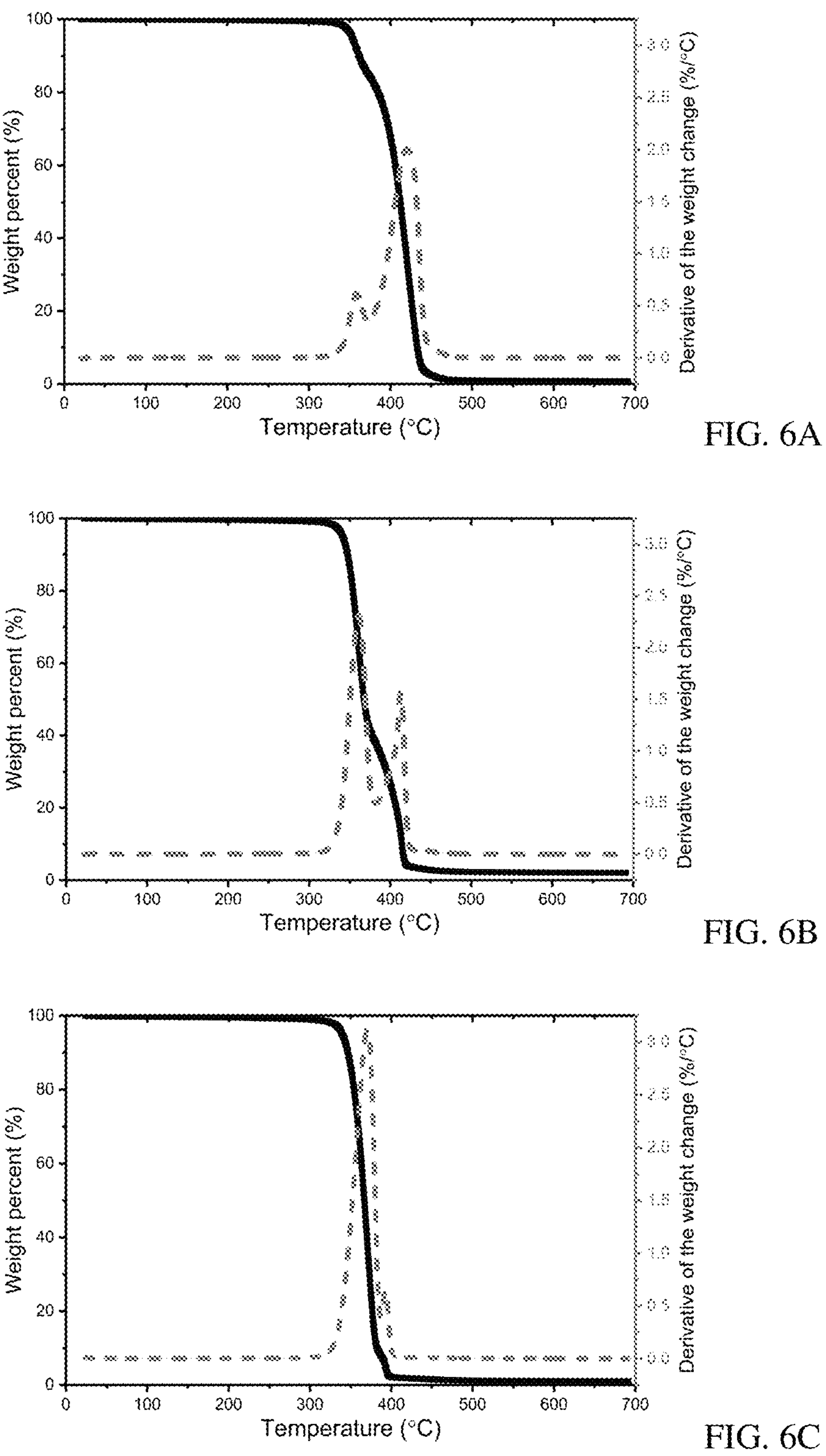
FIG. 6A illustrates TGA weight loss curves (solid lines) and derivatives of the weight loss curves (dashed lines) of PLA-PCL MS with 1:9 molar ratio of PLA to PCL obtained at a 20° C./min heating rate under nitrogen atmosphere.
FIG. 6B illustrates TGA weight loss curves (solid lines) and derivatives of the weight loss curves (dashed lines) of PLA-PCL MS with 5:5 molar ratio of PLA to PCL obtained at a 20° C./min heating rate under nitrogen atmosphere.
FIG. 6C illustrates TGA weight loss curves (solid lines) and derivatives of the weight loss curves (dashed lines) of PLA-PCL MS with 9:1 molar ratio of PLA to PCL obtained at a 20° C./min heating rate under nitrogen atmosphere.

The TGA profiles for PLA-PCL MS with varying molar ratios of PLA to PCL are as shown in FIG. 6A-FIG. 6C. The weight loss curves (solid lines) showed that all three PLA-PCL MS formulations underwent two-step decompositions. PLA-PCL MS with a 1:9 polymer ratio lost 12.3±0.8% weight (n=3) during the first decomposition step, and 84.7±0.6% weight (n=3) during the second step. The mean weight percent loss for the PLA-PCL MS with a 5:5 ratio of PLA to PCL was 56.5±0.9% (n=3) and 38.4±1.1% (n=3) during the first and second thermal degradation steps. PLA-PCL MS with a 9:1 polymer ratio averaged the weight loss of 88.3±1.3% and 7.9±0.3% during the two decomposition steps, respectively. The derivative of the weight change curves (dashed lines) all displayed double peaks.

Figure 7:
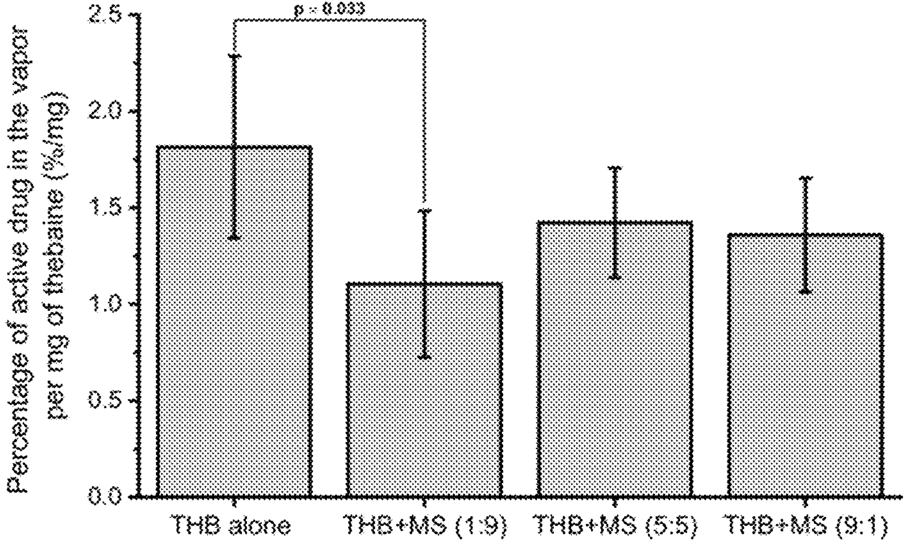
FIG. 7 illustrates analysis of the entrapment of active THB by the three PLA-PCL MS formulations (n=5). Error bars represent+/−standard deviation.

Finally, a vaporization study coupled with HPLC analysis were carried out to compare the drug entrapment capacities of the three PLA-PCL MS formulations. FIG. 7 shows the mean percentage of active drug in the vapor per unit weight of heated THB for the three tested PLA-PCL MS (MS) formulations compared to the negative control (THB alone) group.

The data showed that only PLA-PCL MS with a 1:9 molar ratio of PLA to PCL significantly reduced the amount of active drug in the vapor compared to the negative control (THB alone) group (p=0.033). The average percentage of active THB in the vapor was 1.8±0.5% for THB alone group (n=5), 1.1±0.4% for THB+MS (1:9) group (n=5), 1.4±0.3% for THB+MS (5:5) group (n=5), and 1.4±0.3% for THB+MS (9:1) group (n=5).

3. Comparison of PLA-PCL MS to AC and MPS

Figure 8:
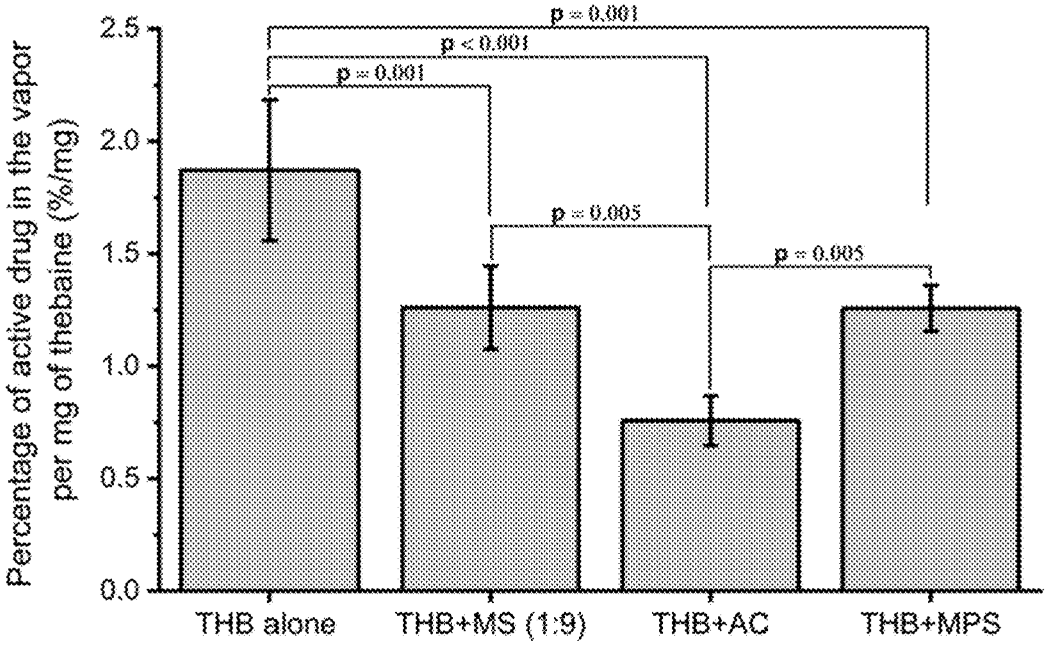
FIG. 8 illustrates analysis of active THB entrapment by the PLA-PCL MS (1:9 molar ratio of PLA to PCL) group in comparison to negative control (THB alone) and positive controls activated carbon (AC) and mesoporous silica (MPS) (n=5). Error bars represent+/−standard deviation.

The ability of PLA-PCL MS with a 1:9 molar ratio of PLA to PCL to entrap active drug during vaporization was compared to that of AC and MPS. The average percentage of active THB in the vapor per mg of drug for MS (1:9)

compared to the negative control (THB alone) and positive controls (AC and MPS) is as shown in FIG. 8.

The data showed that the amount of active drug in the vapor was significantly reduced by PLA-PCL MS ($p=0.001$), AC ($p<0.001$) and MPS ($p=0.001$) compared to the THB alone group. The MS entrapped significantly less active THB than AC ($p=0.005$) but showed no statistical difference from MPS ($p=1.000$). The mean percentage of active drug in the vapor per mg of THB was 1.9±0.3% for THB alone group (n=5), 1.3±0.2% for THB+PLA-PCL MS (1:9) group (n=5), 0.8±0.1% for THB+AC (5:5) group (n=5), and 1.3±0.1% for THB+MPS group (n=5).

Figure 9:
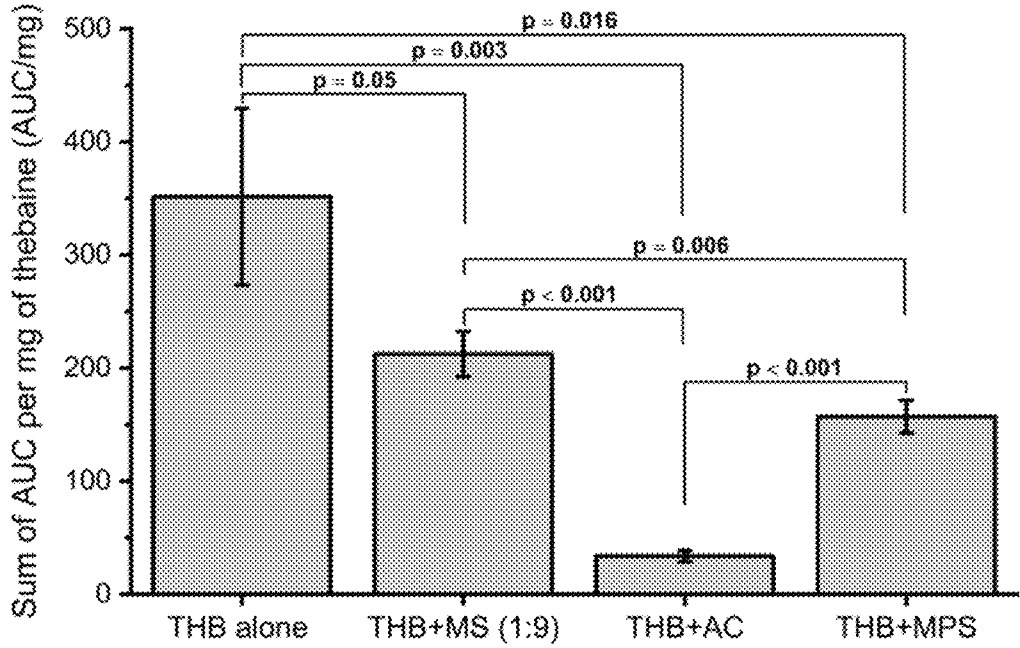
FIG. 9 illustrates analysis of THB thermal decomposition products entrapment by PLA-PCL MS (1:9 molar ratio of PLA to PCL) compared to negative control (THB alone) and positive controls (AC and MPS) (n=5). Error bars represent+/−standard deviation.

The total area under the curve (AUC) per mg of drug was also analysed, which served as a measure of the total amount of vaporized active THB and its thermal degradation products, which was the dominant product in this case. FIG. 9 shows the mean sum of AUC per mg of THB for PLA-PCL MS (MS) (1:9) treatment group and the controls.

The amount of degradation products in the vapor was significantly reduced by PLA-PCL MS ($p<0.001$), AC ($p<0.001$) and MPS ($p<0.001$) compared to the THB alone group. The MS entrapped significantly less thermal decomposition products of THB than AC ($p<0.001$) but were not statistically different from MPS ($p=0.184$). The average sum of AUC per mg of drug was 351.4±78.2% for THB alone group (n=5), 212.4±19.9% for THB+MS (1:9) group (n=5), 33.6±4.9% for THB+AC group (n=5), and 156.9±14.5% for THB+MPS group (n=5).

Next, drug entrapment was assessed using TGA as on orthogonal method to by the PLA-PCL MS in comparison to AC and MPS. Analysis of the changes in mass of THB when heated alone and in mixtures with PLA-PCL MS, AC and MPS over a defined temperature interval allows for quantitative assessment of the drug entrapment by the polymer blend microparticles and the two positive controls. FIG. 10A-FIG. 10D shows the TGA profiles for individual compounds THB, PLA-PCL MS, AC and MPS and FIG. 11A-FIG. 11C shows the TGA profiles for the mixtures of THB with PLA-PCL MS, AC and MPS under oxidizing atmosphere (air).

Figure 12A:
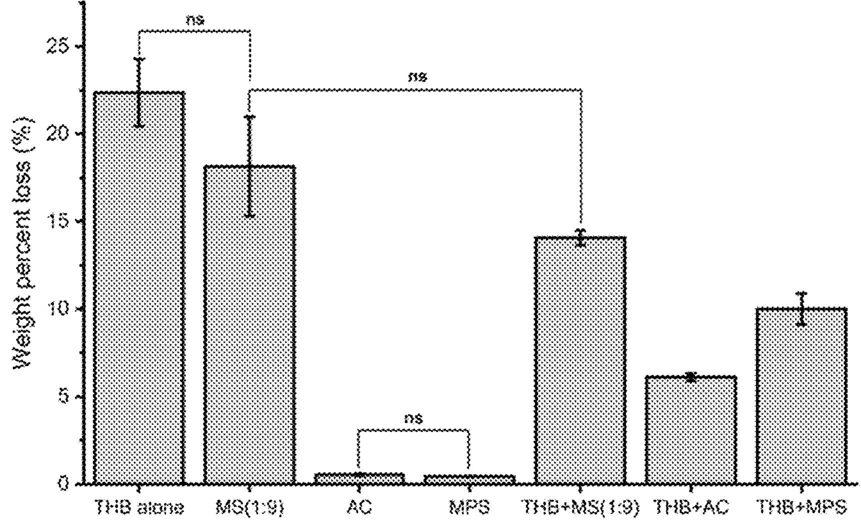
FIG. 12A illustrates an analysis of weight percent loss in the temperature interval from 100° C. to 325° C. for the tested individual compounds and their mixtures.
Figure 12B:
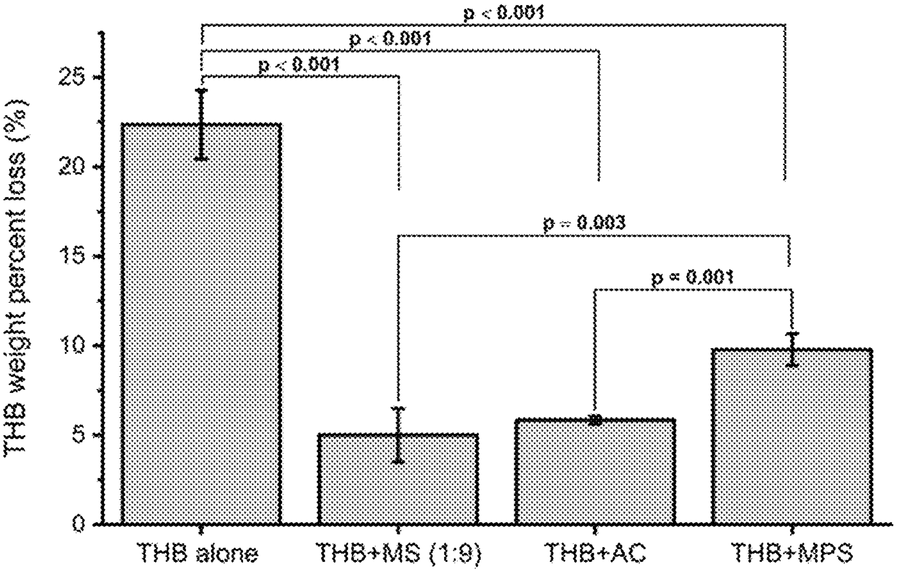
FIG. 12B illustrates an analysis of THB weight percent loss in the temperature interval from 100° C. to 325° C. for the drug alone and the drug mixed with MS, AC and MPS (n=5).

Weight percent loss was analysed over the 100° C.-325° C. temperature range. These temperatures are not high enough to vaporize THB, but they are sufficiently high for inducing thermal decomposition of the drug. Also, in this temperature interval, AC and MPS experience negligibly small mass losses, while THB and PLA-PCL MS lose a similar amount of mass. The percentages of weight lost by THB, MS (1:9), AC, MPS and the mixtures of THB with MS, AC and MPS in the range from 100° C. to 325° C. are illustrated in FIG. 12A.

The data indicated that AC and MPS groups were not significantly different from each other ($p=1.000$). All the other groups showed statistical differences. Therefore, PLA-PCL MS significantly decreased the amount of active drug and its thermal degradation products in the vapor released upon heating of the drug and therefore can potentially be used as an ADF against smoking of common prescription drugs that can be abused.

Those skilled in the art will recognize that numerous modifications can be made to the specific implementations described above. The implementations should not be limited to the particular limitations described. Other implementations may be possible.

We claim:

1. A method of deterring abuse of an oral dosage form of a drug, which can be abused by smoking, which method comprises incorporating into the oral dosage form of the drug a formulation comprising, a physical barrier, which is (i) an additive selected from a molecular sieve, a mesoporous silica, an activated carbon, or a combination thereof, and (ii) a polymeric network of microspheres having an average diameter from about 1.5 μm to about 4.0 μm and comprising a polymeric blend consisting of polylactic acid (PLA) and polycaprolactone (PCL) in a ratio ranging from about 1:9 to about 9:1, wherein, upon heating of the oral dosage form above the melting point of the microspheres, the microspheres melt and entrap the drug, thereby deterring abuse of the oral dosage form of the drug by smoking.

2. The method of claim 1, wherein PLA and PCL are used in a ratio of 1:9, 5:5 or 9:1.

3. The method of claim 2, wherein, when PLA and PCL are used in a ratio of 1:9, the mean diameter of the microspheres is 3.1±0.7 μm, when PLA and PCL are used in a ratio of 5:5, the mean diameter of the microspheres is 2.4±0.7 μm, and when PLA and PCL are used in a ratio of 9:1, the mean diameter of the microspheres is 2.3±0.5 μm.

4. The method of claim 1, wherein the drug is selected from opioid drugs, sedatives, central nervous system (CNS) depressants, CNS stimulants, and hallucinogens.

5. The method of claim 1, wherein the drug is an opioid drug.

* * * * *